(12) United States Patent
Fulmes et al.

(10) Patent No.: US 11,311,420 B1
(45) Date of Patent: *Apr. 26, 2022

(54) APPARATUS FOR WOUND INFECTION PREVENTION

(71) Applicants: Mychailo Fulmes, Brooklyn, NY (US); Ihor Turkevych, Southampton, PA (US); Michael McGough, Southampton, PA (US)

(72) Inventors: Mychailo Fulmes, Brooklyn, NY (US); Ihor Turkevych, Southampton, PA (US); Michael McGough, Southampton, PA (US)

(73) Assignee: Life Sciences, LLC, Wilmington, DE (US)

( * ) Notice: Subject to any disclaimer, the term of this patent is extended or adjusted under 35 U.S.C. 154(b) by 552 days.

This patent is subject to a terminal disclaimer.

(21) Appl. No.: 16/148,876

(22) Filed: Oct. 1, 2018

Related U.S. Application Data

(63) Continuation of application No. 14/193,584, filed on Feb. 28, 2014, now Pat. No. 10,085,892.

(Continued)

(51) Int. Cl.
*A61F 13/00* (2006.01)
*A61F 13/02* (2006.01)
*A61B 17/08* (2006.01)

(52) U.S. Cl.
CPC .. *A61F 13/00068* (2013.01); *A61F 13/00021* (2013.01); *A61F 13/00029* (2013.01);
(Continued)

(58) Field of Classification Search
CPC ............ A61F 13/00068; A61F 13/0223; A61F 13/00029; A61F 13/00034;
(Continued)

(56) References Cited

U.S. PATENT DOCUMENTS

| 3,682,180 A | 8/1972 | Mcfarlane |
| 3,753,439 A | 8/1973 | Brugarolas et al. |

(Continued)

FOREIGN PATENT DOCUMENTS

EP 0604101 A1 6/1994

OTHER PUBLICATIONS

Benedetta Allegranzi et al. and the WHO Guidelines Development Group. Surgical site infections 1: New WHO recommendations on preoperative measures for surgical site infection prevention: an evidence-based global perspective, Lancet Infect Dis 2016: Published online Nov. 2, 2016 http://dx.doi.org/10.1016/S1473-3099(16)30398-X.

(Continued)

*Primary Examiner* — Adam Marcetich
(74) *Attorney, Agent, or Firm* — Michael S. Young IP Law LLC; Michael S. Young

(57) ABSTRACT

A wound healing device and method that greatly reduces the risk of infection of an incision or wound by removing fluid from the subcutaneous skin layers. The wound healing device includes a first portion that is positioned external of, and on top of, the wound. At least one strip, cord, finger, member is in fluid communication at one end with the first portion while the second free end of the at least one strip, cord, finger, member is pushed down into the wound, in between the sutures or staples of a closed incision. Both the first portion and the at least one strip comprise fluid absorbable material for absorbing the wound fluid. The device remains in place for approximately 1-3 days after which it is removed. Upon removal, natural temporary "type of fistulae" are formed in the subcutaneous skin layers to continue draining wound fluids upward for another 1-2 days.

20 Claims, 14 Drawing Sheets

Related U.S. Application Data

(60) Provisional application No. 61/914,720, filed on Dec. 11, 2013, provisional application No. 61/774,272, filed on Mar. 7, 2013.

(52) U.S. Cl.
CPC .. *A61F 13/00034* (2013.01); *A61F 13/00042* (2013.01); *A61F 13/00063* (2013.01); *A61F 13/0203* (2013.01); *A61F 13/0223* (2013.01); A61B 17/085 (2013.01); A61F 2013/00455 (2013.01)

(58) Field of Classification Search
CPC ............ A61F 13/00042; A61F 13/0203; A61F 13/00021; A61F 13/00063; A61F 2013/00455; A61F 2013/15487; A61F 2013/15495; A61F 2013/15504; A61F 2013/15512; A61F 2013/1552; A61F 2013/15528; A61F 2013/15536; A61B 17/085
See application file for complete search history.

(56) References Cited

U.S. PATENT DOCUMENTS

| | | | |
|---|---|---|---|
| 4,250,882 A | 2/1981 | Adair | |
| 4,553,966 A | 11/1985 | Korteweg | |
| 4,815,457 A | 3/1989 | Mazars et al. | |
| 4,917,928 A | 4/1990 | Heinecke | |
| 4,960,467 A * | 10/1990 | Peck | A61B 10/0064 |
| | | | 252/194 |
| 5,053,021 A | 10/1991 | Feibus | |
| 5,078,709 A * | 1/1992 | Siciliano | A61F 13/00042 |
| | | | 602/45 |
| 5,113,871 A * | 5/1992 | Viljanto | A61B 10/02 |
| | | | 600/581 |
| 5,153,040 A | 10/1992 | Faasse, Jr. | |
| 5,180,375 A | 1/1993 | Feibus | |
| 5,266,371 A | 11/1993 | Sugii et al. | |
| 5,358,492 A | 10/1994 | Feibus | |
| 5,531,999 A | 7/1996 | Cartmell et al. | |
| 5,771,967 A * | 6/1998 | Hyman | B64G 1/50 |
| | | | 126/45 |
| 5,809,826 A * | 9/1998 | Baker, Jr. | G01N 27/048 |
| | | | 73/29.01 |
| 5,840,052 A | 11/1998 | Johns | |
| 5,860,259 A * | 1/1999 | Laska | E04B 1/7675 |
| | | | 52/302.3 |
| 5,898,964 A | 5/1999 | Stanley | |
| 5,973,221 A | 10/1999 | Collyer et al. | |
| 6,178,984 B1 * | 1/2001 | Amsellem | A01G 27/005 |
| | | | 137/142 |
| 6,420,622 B1 | 7/2002 | Johnston et al. | |
| 6,432,096 B1 | 8/2002 | McFall et al. | |
| 6,605,068 B2 | 8/2003 | Righetti | |
| 6,884,427 B1 | 4/2005 | Barrows | |
| 6,936,037 B2 | 8/2005 | Bubb et al. | |
| 7,182,758 B2 | 2/2007 | McCraw | |
| 7,619,130 B2 | 11/2009 | Nielsen et al. | |
| 7,709,694 B2 | 5/2010 | Batich et al. | |
| 8,172,818 B2 | 5/2012 | Locke et al. | |
| 9,456,930 B2 | 10/2016 | Zamierowski | |
| 2001/0000796 A1 | 5/2001 | Osborn et al. | |
| 2001/0027347 A1 | 10/2001 | Rousseau | |
| 2003/0004579 A1 | 1/2003 | Rousseau et al. | |
| 2003/0068646 A1 * | 4/2003 | Singh | B01L 3/502723 |
| | | | 435/7.1 |
| 2003/0093075 A1 | 5/2003 | Levinson | |
| 2003/0191442 A1 | 10/2003 | Bewick-Sonntag et al. | |
| 2004/0077103 A1 * | 4/2004 | Buechler | B01L 3/50273 |
| | | | 436/514 |
| 2004/0087980 A1 | 5/2004 | Ford et al. | |
| 2004/0106941 A1 * | 6/2004 | Roe | A61B 5/15142 |
| | | | 606/181 |
| 2004/0249328 A1 | 12/2004 | Linnane et al. | |
| 2004/0262570 A1 * | 12/2004 | Radomyselski | D06L 1/10 |
| | | | 252/180 |
| 2005/0033251 A1 | 2/2005 | Toreki et al. | |
| 2005/0107731 A1 | 5/2005 | Sessions | |
| 2005/0107756 A1 * | 5/2005 | McCraw | A61M 27/00 |
| | | | 604/317 |
| 2005/0148920 A1 | 7/2005 | Addison | |
| 2005/0273066 A1 | 12/2005 | Wittmann | |
| 2006/0015019 A1 * | 1/2006 | Watt | A61M 1/0025 |
| | | | 600/309 |
| 2006/0041247 A1 | 2/2006 | Petrosenko et al. | |
| 2006/0162072 A1 | 7/2006 | Tenenbaum et al. | |
| 2006/0163152 A1 | 7/2006 | Ward et al. | |
| 2006/0241689 A1 | 10/2006 | Leiboff et al. | |
| 2007/0038172 A1 * | 2/2007 | Zamierowski | A61M 1/0088 |
| | | | 604/20 |
| 2007/0224087 A1 * | 9/2007 | Ding | B01L 3/502792 |
| | | | 422/83 |
| 2007/0265585 A1 * | 11/2007 | Joshi | A61M 1/962 |
| | | | 604/313 |
| 2008/0132819 A1 | 6/2008 | Radl et al. | |
| 2008/0167593 A1 | 7/2008 | Fleischmann | |
| 2008/0206293 A1 | 8/2008 | Toreki et al. | |
| 2008/0287892 A1 | 11/2008 | Khan et al. | |
| 2009/0025160 A1 * | 1/2009 | Ikeda | G01N 21/15 |
| | | | 15/102 |
| 2009/0105731 A1 | 4/2009 | Priewe | |
| 2009/0280182 A1 | 11/2009 | Beck et al. | |
| 2009/0313762 A1 | 12/2009 | Boutwell | |
| 2010/0036334 A1 * | 2/2010 | Heagle | A61M 1/0088 |
| | | | 604/319 |
| 2010/0106122 A1 | 4/2010 | Clemens | |
| 2010/0174250 A1 | 7/2010 | Hu et al. | |
| 2010/0179515 A1 * | 7/2010 | Swain | A61M 1/0088 |
| | | | 604/543 |
| 2010/0210745 A1 | 8/2010 | McDaniel et al. | |
| 2010/0268128 A1 | 10/2010 | Randolph | |
| 2010/0318047 A1 | 12/2010 | Ducker et al. | |
| 2010/0324516 A1 * | 12/2010 | Braga | A61F 13/00 |
| | | | 604/378 |
| 2011/0015619 A1 | 1/2011 | Svedman et al. | |
| 2011/0144667 A1 | 6/2011 | Horton et al. | |
| 2011/0208145 A1 | 8/2011 | Zhang et al. | |
| 2011/0240064 A1 | 10/2011 | Wales et al. | |
| 2011/0270201 A1 | 11/2011 | Bubb et al. | |
| 2012/0077886 A1 | 3/2012 | Scholz et al. | |
| 2012/0093759 A1 | 4/2012 | Vachon | |
| 2012/0130327 A1 * | 5/2012 | Marquez | A61M 1/0088 |
| | | | 604/319 |
| 2012/0186016 A1 | 7/2012 | Martin | |
| 2012/0253302 A1 | 10/2012 | Corley | |
| 2013/0035649 A1 | 2/2013 | Locke et al. | |
| 2013/0151223 A1 | 6/2013 | Zamierowski et al. | |
| 2013/0190408 A1 | 7/2013 | Scholz et al. | |
| 2013/0197459 A1 | 8/2013 | Brezoczky et al. | |
| 2013/0217284 A1 | 8/2013 | Wang | |
| 2013/0274629 A1 | 10/2013 | Duesterhoft et al. | |
| 2014/0031735 A1 | 1/2014 | Zurovcik | |
| 2015/0157774 A1 | 6/2015 | Zamierowski | |
| 2016/0270963 A1 | 9/2016 | Zamierowski et al. | |
| 2016/0346444 A1 | 12/2016 | Zamierowski | |

OTHER PUBLICATIONS

Benedetta Allegranzi et al. and the WHO Guidelines Development Group. Surgical site infections 2: New WHO recommendations on intraoperative and postoperative measures for surgical site infection prevention: an evidence-based global perspective, Lancet Infect Dis 2016: Published online Nov. 2, 2016 http://dx.doi.org/10.1016/S1473-3099(16)30402-9.

Braen, et al. Manual of Emergency Medicine, 2011, p. 464.

Frederick E. Jackson and Richard A. Pratt. Technical report: A silicone rubber suction drain for drainage of subdural hematomas. Surgery, Oct. 1971: vol. 70, No. 4, 578-579.

(56) References Cited

OTHER PUBLICATIONS

Fulmes, et al. Packing the Closed Incision After Open Colon Resection Can Decrease the Risk of Wound Infection. A Pilot Study, Lehigh Valley Health Network, Department of Surgery, 2012, 3 pages.
Harper, W.W. The Treatment of Injuries to the Soft Parts of the Hand, International Journal of Surgery, vol. 21, Oct. 1908, pp. 303-304.
International Search Report for corresponding PCT Application No. PCT/US2014/019519 dated Jun. 3, 2014.
International Written Opinion for corresponding PCT Application No. PCT/US2014/019519 dated Jun. 3, 2014.
Lee, et al. Using a Full-depth Wound Drainage System to Decrease Wound Infection Rates in the Morbidly Obese, Obesity Surgery, 1991, 1: 435-438.
McGreal, Gerald T., et al. Antiseptic wick: does it reduce the incidence of wound infection following appendectomy, World journal of surgery 26.5 (2002): 631-634.
Medline, Todays Wound Care Treatments, May 2013.

\* cited by examiner

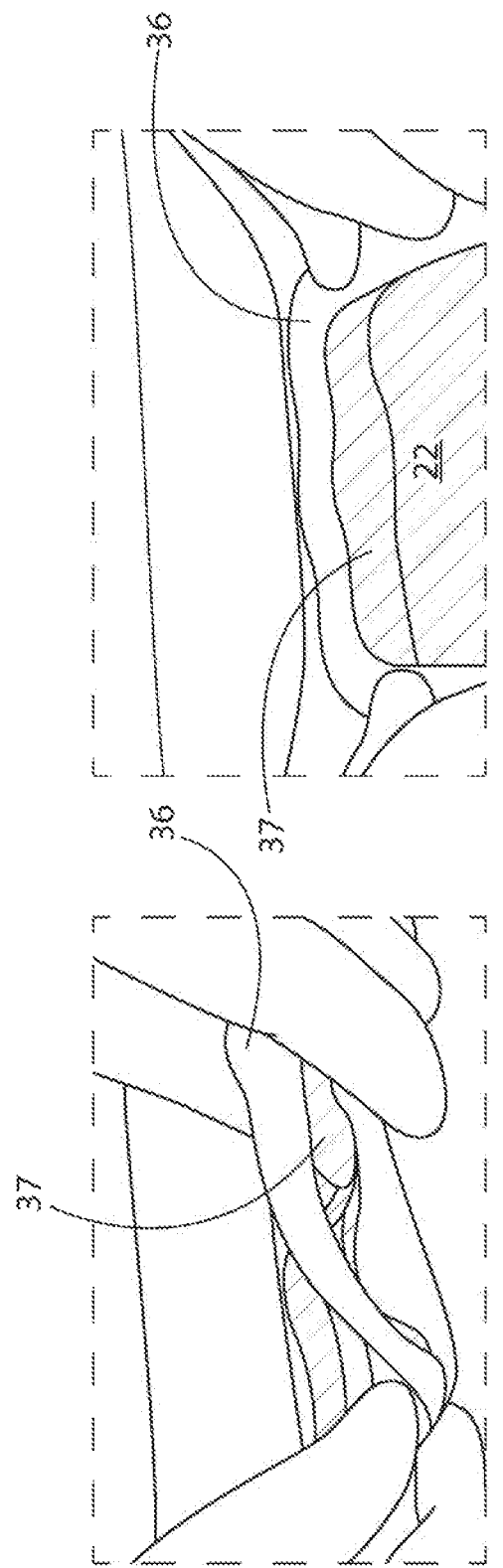
FIG. 4J
FIG. 4K
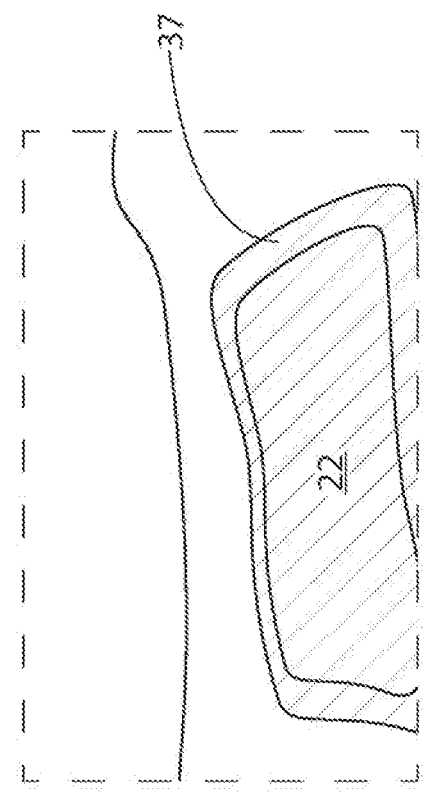
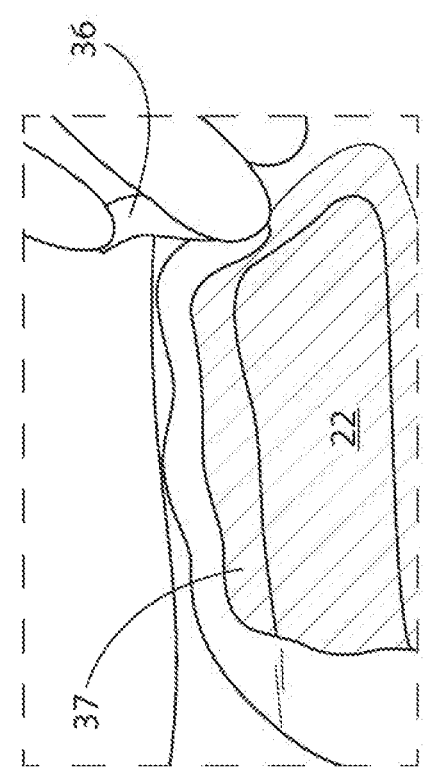
FIG. 4L
FIG. 4M

APPARATUS FOR WOUND INFECTION PREVENTION

CROSS-REFERENCE TO RELATED APPLICATIONS

This nonprovisional application is co-pending with U.S. patent application Ser. No. 14/193,584 filed on Feb. 28, 2014 entitled APPARATUS & METHOD FOR WOUND INFECTION PREVENTION. This nonprovisional application claims priority to U.S. patent application Ser. No. 14/193,584 entitled APPARATUS & METHOD FOR WOUND INFECTION PREVENTION that claims the benefit under 35 U.S.C. § 119(e) of both Application Ser. No. 61/774,272 filed on Mar. 7, 2013 entitled METHOD OF WOUND INFECTION PREVENTION AND CLEAN KIT and Application Ser. No. 61/914,720 filed on Dec. 11, 2013 entitled APPARATUS AND METHOD FOR WOUND INFECTION PREVENTION, and all of the entire disclosures of the patent applications are incorporated by reference herein.

BACKGROUND

The present invention relates generally to apparatus and methods for treating wounds, and more particularly, to an apparatus and method for healing closed incisions following surgery.

America wastes over a billion dollars annually, on post-operative surgical site infection expenses. These surgeries have an acknowledged overall infection rate of between 15%-30%. Surgical site infection slows the recovery rate for patients and adds additional health costs with prolonged hospital treatment, additional home care, physician office and emergency room visits expenses.

Typically, physicians often respond to the risk of wound infection with the "open wound" technique, subjecting patients to psychological torment of the patient knowing they have an open wound, restricting them from normal activity. The patient is left with a hole in their body open to the outside; which requires additional health maintenance including additional dressing changes by visiting nurses, additional physician consultation and additional high cost of vacuum device usually for a week or longer.

Physicians, attempts to avoid an open wound, will often install a drainage device in the patient. This is accomplished by placing a plastic tube into the patient, horizontally along the fascia layer and closing the wound around the tube. The most common drains; the "J-Drain", and "Penrose Drain", do not remove fluid from all three layers of skin, have a tendency to clog up and can even increase the production of additional fluid in patients; at times making the infection and recovery issues worse. The drains must then eventually be removed by surgeon, sometimes weeks after surgery. Research shows these drains have a poor rate of success with some studies showing an actual increase in patient complications.

Patients enduring the traditional old fashioned healing systems frequently require weeks to recover, extensive follow-up treatments and procedures and have increased the risk of complications and even death.

Recently, open wound "negative pressure" treatments are now also being touted as the answer for closed incision as well as open wound infection preventative treatments; this treatment simply removes excess fluid from cutaneous areas from the outer skin level. Negative pressure treatments fail to effectively address the underlining cause of surgical site infection (SSI) in closed incisions. The negative pressure VAC (vacuum) systems are also very expensive and are physician and nurse-labor intensive. The data surrounding the VAC systems appears to be mixed and studies appear to show that these systems involve patients with fewer high risk factors prior to surgery.

SSI infections may occur from the following, but not limited to: colorectal, general surgery, OBGYN, urology, vascular, neurosurgery and other procedures. The incisions or wounds closed following their respective surgeries are susceptible to high infection rates and slow patient recovery periods which also impact the physician, staff, hospital, insurer, etc. Moreover, SSI costs hospitals billions of dollars every year in the U.S. and insurance companies do not reimburse hospitals for maladies caused by infection, and corresponding complications, due to surgical site infection.

Thus, there remains a need for an apparatus and associated method that enables the physician to close the wound without significantly increasing the risk of surgical site infection to the patient, thereby being able to safely close more patients following surgery and improving their lives. The apparatus and associated method is easy to remove from the patient and is a cost effective solution.

All references cited herein are incorporated herein by reference in their entireties.

BRIEF SUMMARY

A wound healing device for applying within an incision or wound is disclosed. The wound healing device comprises: a first portion (e.g., a dressing, bandage, etc.) that is applied over the incision or wound (e.g., open or closed), wherein the first portion comprises a fluid absorbent material (e.g., any natural or synthetic material, such but not limited to: cotton, Teflon, nylon, packing material, etc.); a second portion (e.g., strip, loop, tab, cord, appendage, tentacle, finger, etc.) that is in fluid communication and comprises a fluid absorbent material or materials material (e.g., any natural or synthetic material, such but not limited to: cotton, Teflon, nylon, packing material, etc.) with the first portion at a first end of the second portion and a second end of the second portion that is positioned within the wound in the subcutaneous skin layer, wherein the second portion comprises a fluid absorbent material (e.g., any natural or synthetic material, such but not limited to cotton, nylon, packing material, etc.).

A method for wound healing that greatly reduces the chances for infection of an incision or wound (e.g., open or closed) of a patient is disclosed. The method comprises: inserting one end of at least one fluid absorbing material (e.g., any natural or synthetic material, such but not limited to cotton, Teflon, nylon, packing material, etc.) inside the incision or wound; positioning a second end of said at least one fluid absorbing material (e.g., strip, loop, tab, cord, appendage, tentacle, finger, etc.) which in itself permits the inclusion of air into the incision, to be in fluid communication with another fluid absorbent material (e.g., a dressing, bandage, etc. and also comprising any natural or synthetic material, such but not limited to cotton, Teflon, nylon, packing material, etc.) that is positioned external of the patient and over top of the incision or wound; and maintaining said at least one fluid absorbing material and said another fluid absorbent material within and top of the incision or wound respectively, for approximately 1-3 days for conveying fluid out of the incision or wound and into the another fluid absorbent material. Because of the communication between the (e.g., strip, loop, tab, cord, appendage, tentacle, finger, etc.) and the outer dressing, the (e.g., strip, loop, tab, cord, appendage, tentacle, finger, etc.) cannot be accidentally left inside the patient.

A wound healing device for applying within an incision or wound (e.g., open or closed) is disclosed. The wound healing device comprises: at least one fluid absorbent material (e.g., any natural or synthetic material, such but not limited to: cotton, Teflon, nylon, packing material, etc.) formed into a strand (e.g., strip, loop, tab, cord, appendage, tentacle, finger, etc.) having a first end that is positioned within the wound or incision in the subcutaneous skin layer and wherein the strand further comprises a second free end that protrudes out of the wound or incision.

A method for wound healing that greatly reduces the chances for infection of an incision or wound (e.g., open or closed) of a patient is disclosed. The method comprises: forming at least one strand of a fluid absorbing material (e.g., any natural or synthetic material, such but not limited to cotton, Teflon, nylon, packing material, etc.); inserting a first end of said at least one strand (e.g., strip, loop, tab, cord, appendage, tentacle, finger, etc.) inside the incision or wound; positioning a second free end of said at least one strand to be positioned external of the patient; and maintaining said first end of said at least one strand within the incision or wound for approximately 1-3 days for conveying fluid out of the incision or wound and into said strand.

BRIEF DESCRIPTION OF THE SEVERAL VIEWS OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 4A-4M depict a surgeon or other healthcare technician applying the wound healing device of the present invention;

DETAILED DESCRIPTION

Figure 1A:
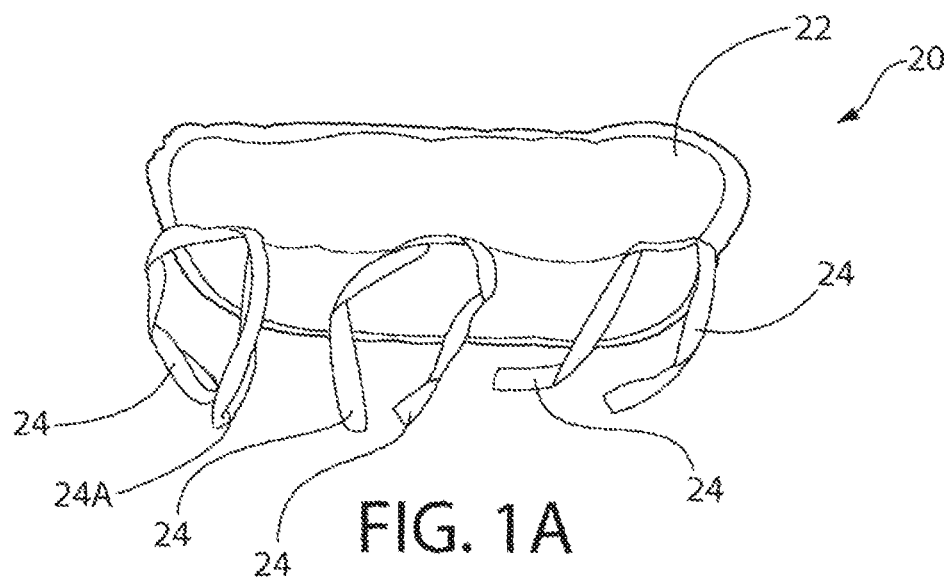
FIG. 1A is bottom view of the wound healing device of the present invention.

Referring now to the figures, wherein like reference numerals represent like parts throughout the several views, exemplary embodiments of the present disclosure will be described in detail. Throughout this description, various components may be identified having specific values, these values are provided as exemplary embodiments and should not be limiting of various concepts of the present invention as many comparable sizes and/or values may be implemented.

The wound healing device (WHD) 20 of the present application absorbs fluid from all three layers of skin, removes fluid where infection is most common—along the incision. The WHD 20 does not clog, does not involve making additional holes in patient and exhibits the highest success rate of any infection reduction system on the highest infection risk patients—patients with multiple additional high risk factors including but not limited to: contaminated incision, diabetes, and malnutrition. As will be discussed in detail, the WHD 20 is a complete fluid absorption system.

As will also be discussed below, the WHD 20 is completely removed from the patient without re-stitching or stapling usually two days following surgery. In many patients once the WHD 20 is removed, no other dressings are necessary. In most cases where an additional light dressing is required, it is usually removed within another day or two.

One of the key features of the WHD 20, as will also be discussed below, is that it is the only device that absorbs fluid and infectious materials at the source during and after the source has formed and the WHD 20 moves the fluid and materials out of the body. Recent data using the WHD 20 cites the infection rate using at 4.2% and in cases where infection did occur, the infection was less severe and covered a smaller area. This data is virtually identical to the probe techniques studies where the patient's wound is cleaned daily with a deep insertion of cotton swabs, for five days following surgery. The probe methodology data is very similar to that related to the WHD 20; with infection rates of 3% and 4% and patients' hospital stays being reduced from 7 to 5 days, per patient. However, even though the probe technique is highly effective, it still requires daily cleaning of wound by physician for five days, and involves significant patient discomfort. It is a labor intensive solution. In contrast, the WHD 20 offers virtually identical results, using very similar concept but without the need of extensive physician labor, potentially high patient discomfort and mental anguish and still only removes the fluid and potentially infectious material after it has collected subcutaneously.

Figure 1B:
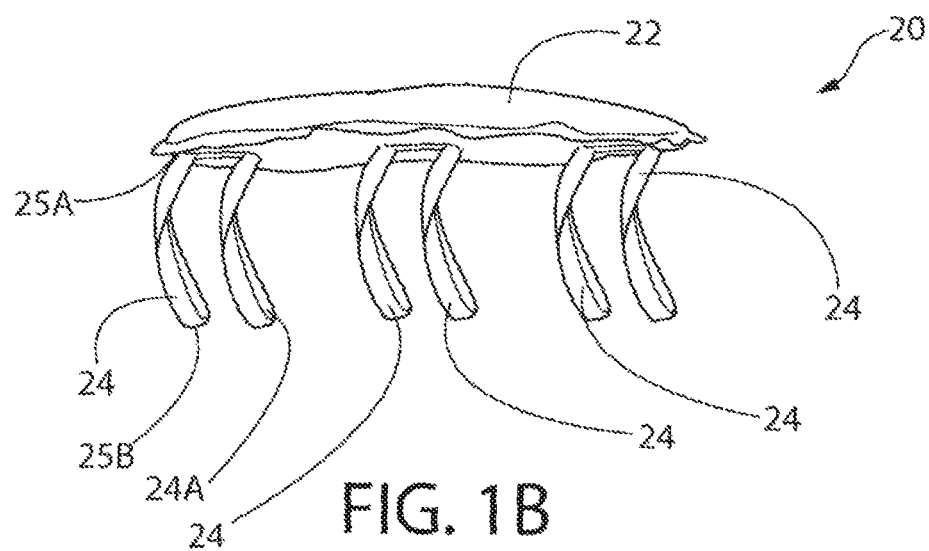
FIG. 1B is a side view of the wound healing device of the present invention.
Figure 1C:
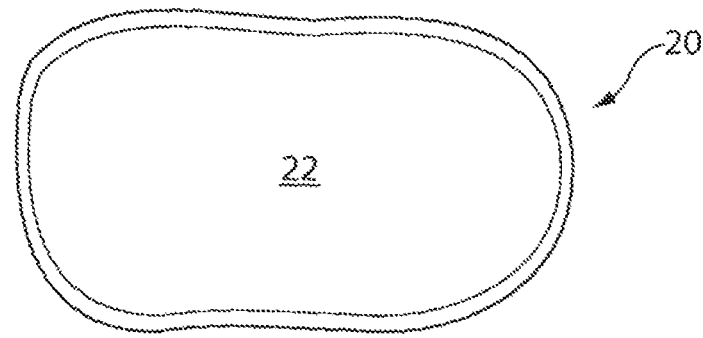
FIG. 1C is top view of the wound healing device.

The preferred embodiment of the WHD 20 (see FIGS. 1A-1C) comprises a first portion 22 that is positioned on top of the patient's skin over the wound. This first portion 22 may referred to as a "dressing". The dressing 22 may comprise any material, either natural or synthetic, or a combination, that can absorb fluids; for example, but not limited to, cotton, Teflon, nylon, packing material, etc. Although FIG. 1A depicts the dressing 22 as comprising a rounded rectangular shape, the dressing 22 is not limited to that shape and may assume any shape or size but as long as it comprises a fluid-absorbing characteristic. The dressing 22 may comprise a single layer or multi-layered construction, and may also be in combination with the use of non-adhering and/or medicated bandage materials and/or materials that control the direction of wicking of liquids.

In fluid communication with the first portion 22 is a second portion 24 that may comprise at least strip 24 that also comprises a fluid-absorbing characteristic. This second portion or strip 24 may comprise a single element of fluid-absorbing characteristic or it may comprise a looped construction, such as that shown by 24A in FIG. 1A. It should be understood that the physical construction of the strip 24 can vary and can be referred to using any number of terms, such as but not limited to, strip, loop, tab, cord, appendage, tentacle, finger, etc. but as long as the strip 24 comprises a fluid-absorbing characteristic. The composition of the strip 24 may comprise any natural or synthetic material such as, but not limited to, cotton, nylon, etc. By way of example only, six strips 24 are shown in fluid communication with the first portion 22. It is also within the broadest scope of the invention to include materials that control the direction of wicking of liquids. This may also be in combination with the use of non-adhering and/or medicated bandage materials. Moreover, it also within the broadest scope of the invention wherein each of the second portion or strips 24 may comprise a tong-like, or comb-like, form to guide or assist in placing or positioning them within in an open or closed wound or incision.

Figure 12:
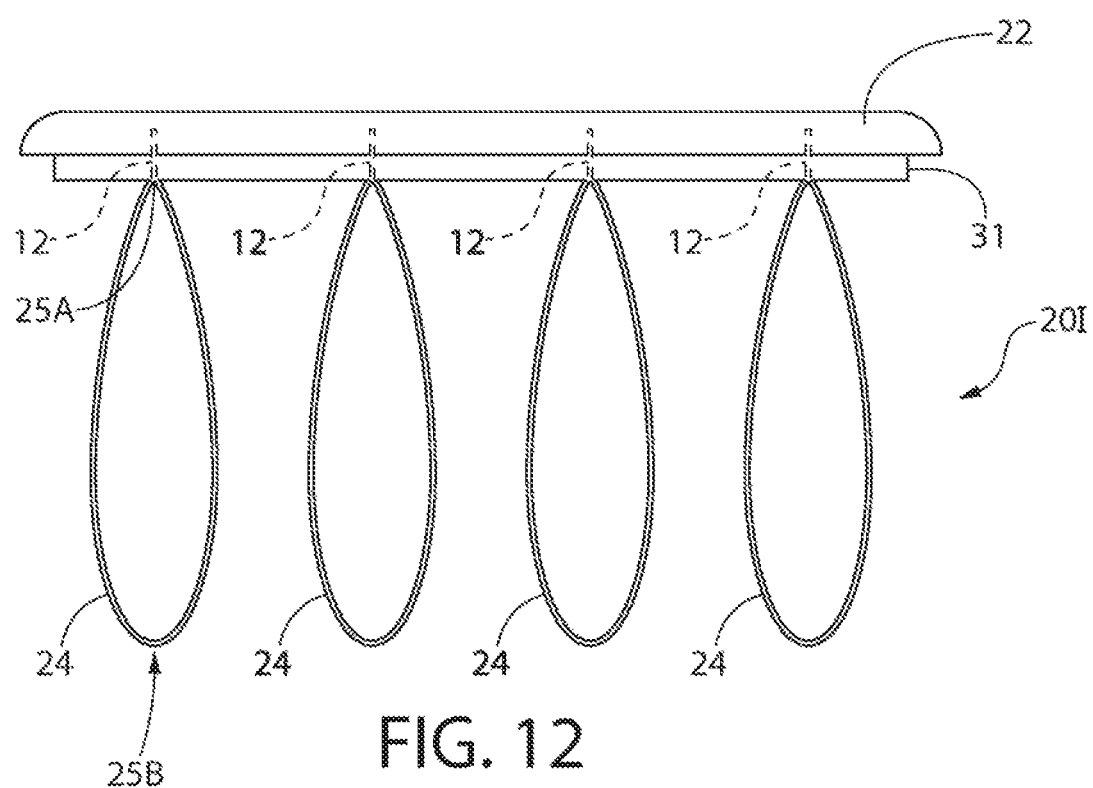
FIG. 12 depicts a tenth embodiment of the present invention wherein the absorbent members are not in direct contact with the dressing but wherein fluids absorbed into the absorbent members can jump or leap into the dressing.

The fluid communication of the second portion 24 to the first portion 22 can be achieved in several ways, one of which is by stitching or via any other method of physically-connecting the first 22 and a first end 25A of the second portion 24, as shown by way of example only in FIG. 1A. However, it is within the broadest scope of the present invention 20 to include the conveyance of fluid from the second portion 24 into the first 22 by way of the fluid "wicking" across a slight gap between an end of the second portion 24 and the first portion 22. This is shown most clearly in FIG. 12 where fluid 12 absorbed into the second portion 24 "leaps" or "jumps" from the extreme end of the second portion 24 through a spacer 31, that physically separates the second portion 24 from the first portion 22, and is finally absorbed into the first portion 22. Thus, the use absorbent members 24 that are not directly in contact with the bandage 22 are within the broadest scope of the invention 20.

The length of the second portion 24 is approximately 2-3 inches, although the length could vary to 4 inches or even 8 inches, depending upon the size of the patient.

Figure 3A:
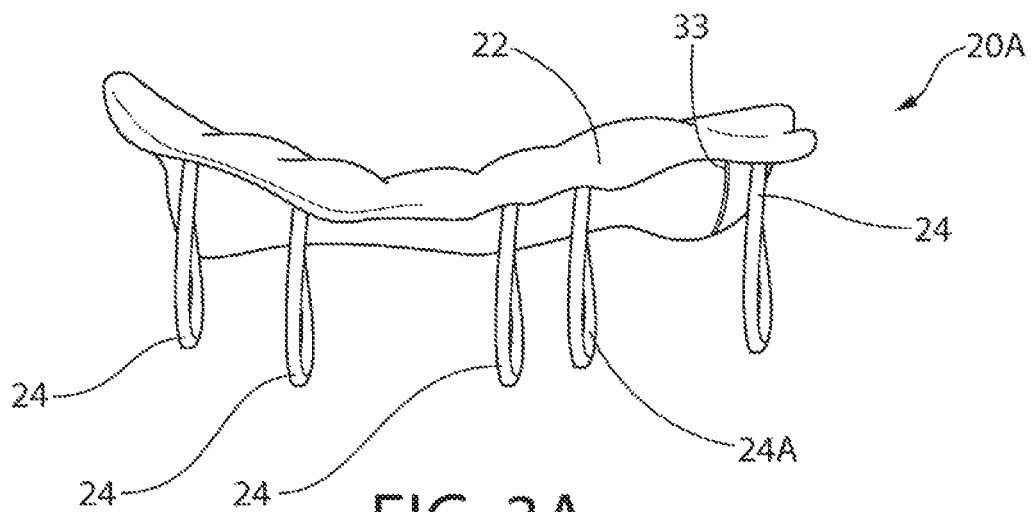
FIG. 3A is a second more simplified embodiment of the wound healing device.
Figure 3B:
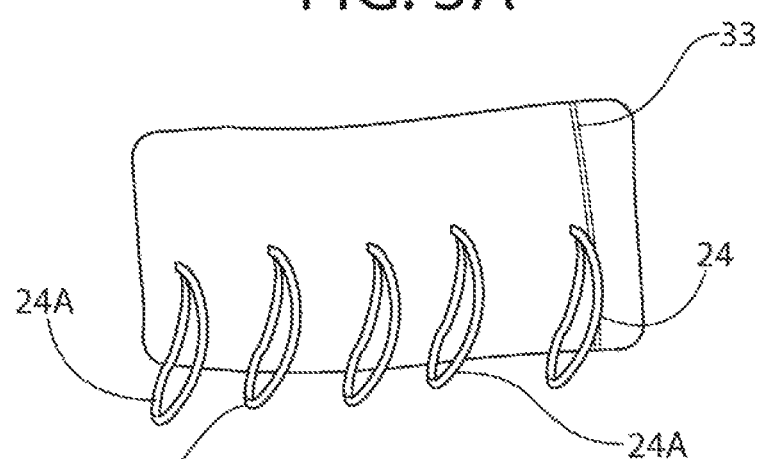
FIG. 3B is bottom view of the second embodiment.
Figure 3C:
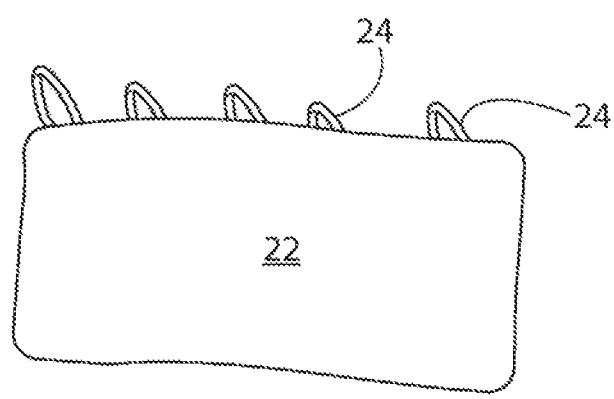
FIG. 3C is a top view of the second embodiment.

FIGS. 3A-3C shown a second, more simplified version of the WHD 20A wherein the first portion 22 comprises a swath of gauze that can be folded into a multi-layer construction and then closed 33 (e.g., stitched) to avoid the first portion 22 from unraveling. Other than that, the WHD 20A operates in the same manner as the WHD 20.

Figure 2A:
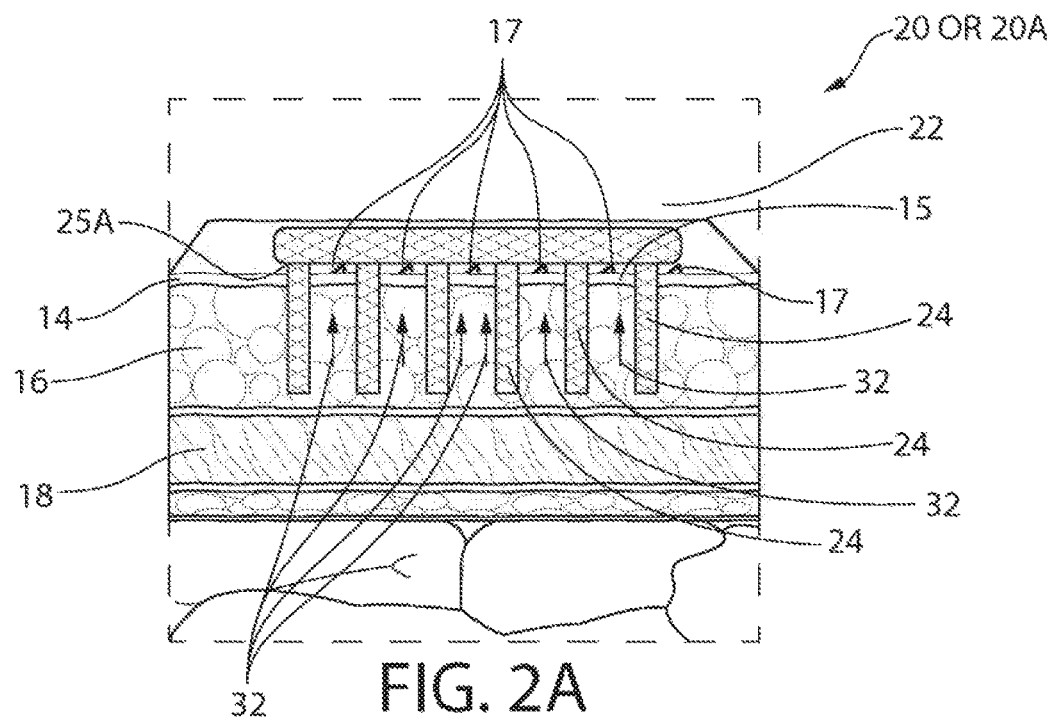
FIG. 2A is a functional diagram of the wound healing device in place in the closed incision or wound (e.g., in a patient's abdominal wall)

FIG. 2A depicts a functional diagram of how the WHD 20/20A works when installed in the wound of the patient. In particular, the surgeon or other healthcare attendant pushes each strip 24 through a portion of the closed incision, in between the wound staples or sutures. By way of example only, the WHD 20/20A shown in FIG. 2A shows the invention with six strips 24 positioned deep inside the closed incision 15 and positioned in the subcutaneous layer tissue 16 above the muscle 18. The first portion (dressing) 22 is positioned on the outer skin 14 directly over the closed incision 15. Fluids that form in this layer are absorbed by the strips 24 and are drawn upward, as shown by arrows 32, out of the skin layers 14/16 and into the first portion (dressing) 22. By removing fluid from these skin layers immediately, the chances for infection are greatly reduced.

Figure 2B:
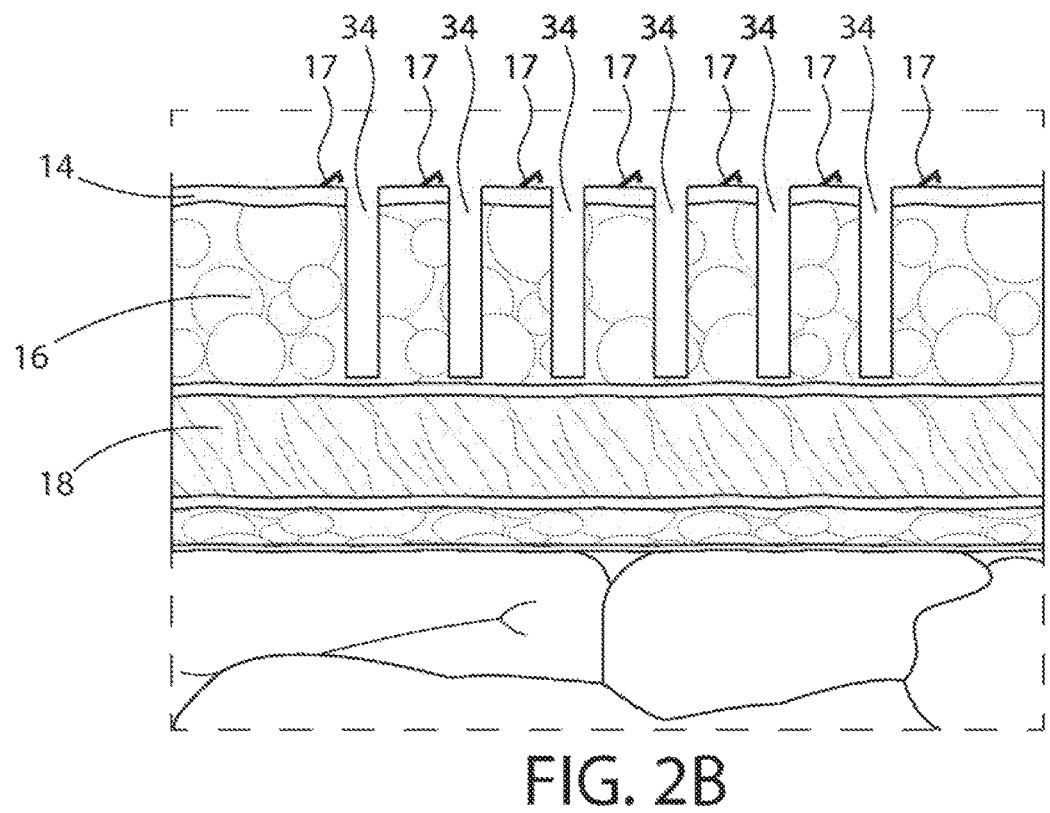
FIG. 2B is a functional diagram of the closed incision following the removal of the wound healing device, showing the formation of type of fistulae in the subcutaneous tissue.

Moreover, upon removal of the WHD 20/20A from the wound in approximately 1-3 days, removal of the strips 24 leaves behind respective "type of fistulae" 34 (see FIG. 2B) within the subcutaneous skin 16 and skin 14 layers. These type of fistulae provide temporary "channels" that permit fluid in the subcutaneous layer 16 to continue to escape upward for a finite time, after removal of the WHD 20/20A, further draining this layer 16 of fluid, and allowing air to enter the wound. In particular, once the WHD 20/20A is removed from the wound 15, a conventional bandage (not shown) is placed over the wound 15. These types of fistulae 34 continue to drain fluid upward towards the conventional bandage, thereby removing even more fluid from the subcutaneous layer 16. Eventually, these type of fistulae 34 naturally close, from the bottom upward, after a few additional days (e.g., 1-2 days) following the removal of the apparatus but they facilitate in draining the subcutaneous layer 16 even more. Thus, the WHD 20/20A also provides temporary draining channels for such fluid that are not formed in the subcutaneous layer 16 by other conventional draining equipment. These types of fistulae 34 serve as a natural drainage system that work in conjunction with the patient's normal healing process and the subsequent closure of the fistula.

FIGS. 4A-4M depict an exemplary WHD 20/20A application process. Although these figures show the use of only two loops 24A, it should be understood that this is simply by way of example and that just one, or more than two strips/loops could be used.

After the surgery, in the domain of sutures or staples 17 of the skin 14 of the subcutaneous, of the subcutaneous 16, and of the fascia, the wound and subject area 15, may be contaminated or clean contaminated or infected wound in which liquid may accumulate and/or colonize bacteriologically, collecting from any and or all layers.

As mentioned earlier, the absorbent dressing 22 is located on the surface of the wound 15 and subject area. Transfer of liquid and waste material from the wound and subject area to the dressing 22 is realized by capillary transfer and any other method of transfer of the absorbent strip, loop, cord or tube or appendage 24 connected or adjacent to the dressing 22 to facilitate the transfer of liquid and material from the wound area dressing 22 is provided with one or more strip, loop, cord or tube or appendage 24 which is, or is located in the area of the wound 15, infected or potentially infected area and therefore facilitates the flow of liquid and bodily waste materials from the subcutaneous 16 to the dressing absorbent material 22 outside the patient body.

The facilitation of the liquid and bodily materials especially from the incision wound 15, infected or potentially infected area or injury area, from potentially any and all subcutaneous areas and levels 16, into absorbent or liquid extractable strips, loops, cords, tubes or absorbent appendage 24 towards and into the adjacent or attached absorbent materials external to the body.

Figure 4A:
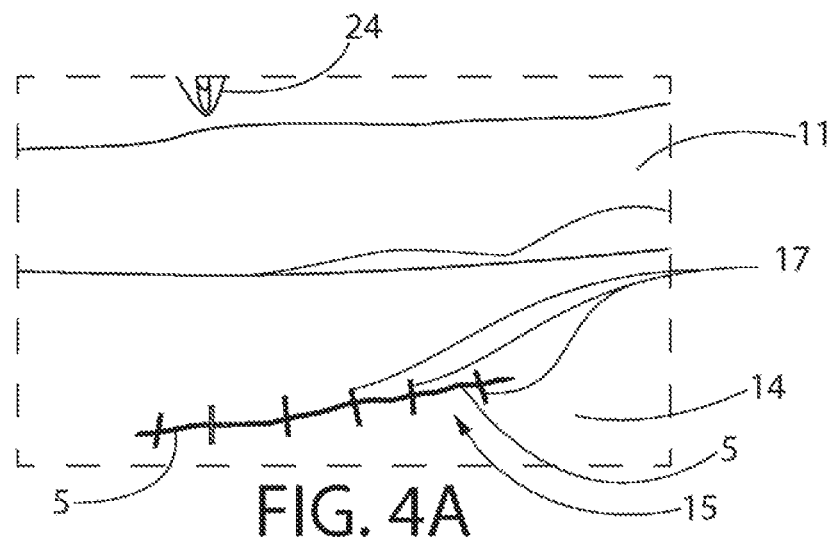

In particular, FIG. 4A shows a wound 15 in the skin 14 closed with staples 17, where gaps 19 between the staples 17 allow the passage of the strips 24, as discussed below; the extreme end (i.e., second end 25B) of one strip 24 can be seen at the top of FIG. 4A, being moved over a surgical covering 11.

Figure 4B:
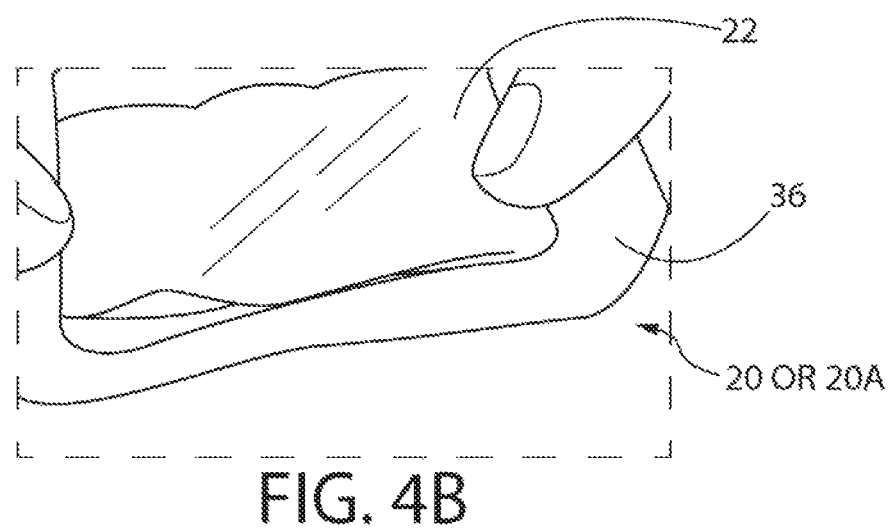

FIG. 4B depicts the WHD 20/20A being positioned over the wound 15 (not visible in FIG. 4B); it should be noted that the WHD 20/20A includes an adhesive border (not shown) which is covered by a release border 36 along the edge of the first portion 22.

Figure 4C:
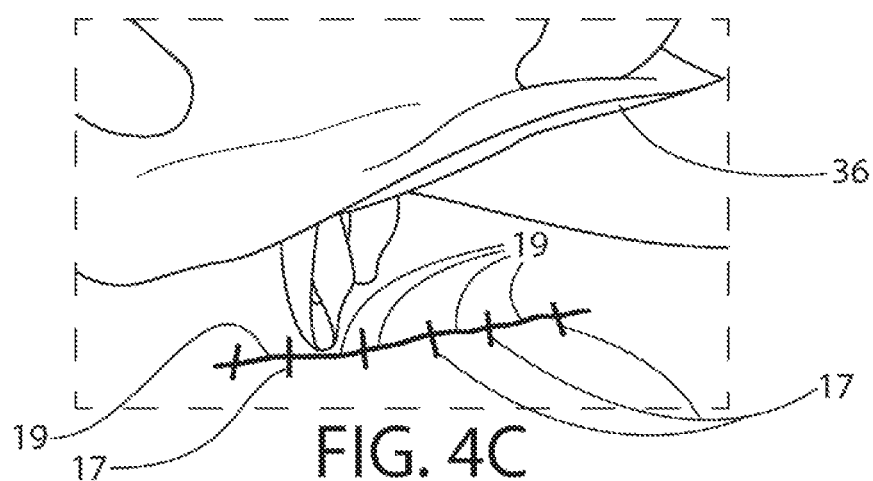
Figure 4D:
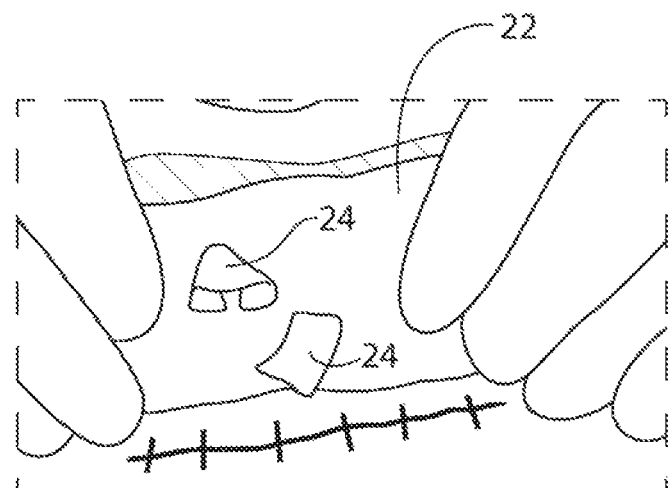
Figure 4E:
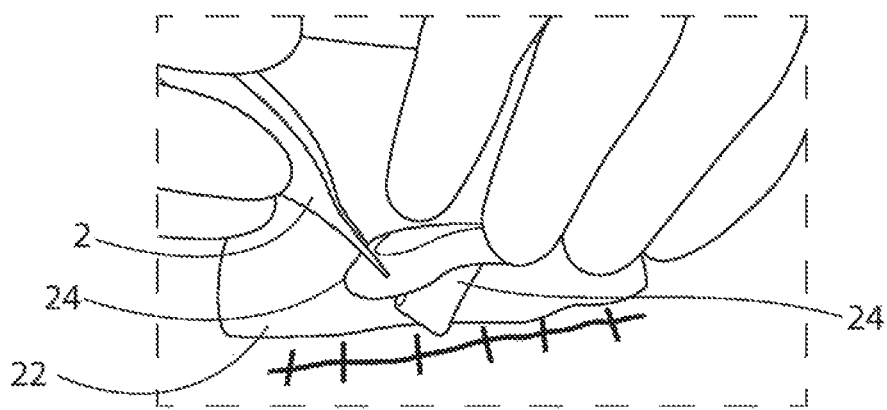
Figure 4F:
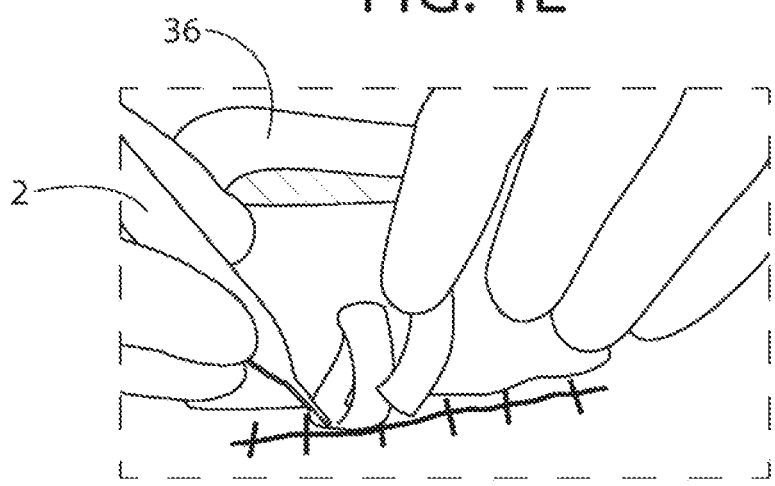

FIG. 4C shows the surgeon or other healthcare attendant manipulating the WHD 20/20A such that one of the strips 24 is positioned over a gap 19 between staples 17. FIG. 4D shows the surgeon or healthcare attendant (hereinafter "surgeon") further manipulating the WHD 20/20A in order to properly position one of the strips 24 over a gap 19 in the wound 15 between staples 17. FIG. 4E shows the surgeon seizing one of the strips 24 with a clamp 2 in preparation to push the strip 24 into the gap 19; in FIG. 4F, the surgeon is pushing the free end of the strip 24 into a gap 19 in the wound 15.

Figure 4G:
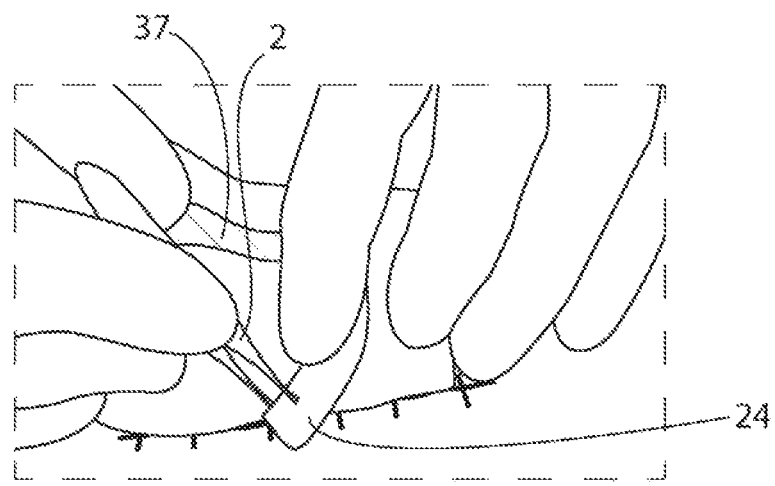
Figure 4H:
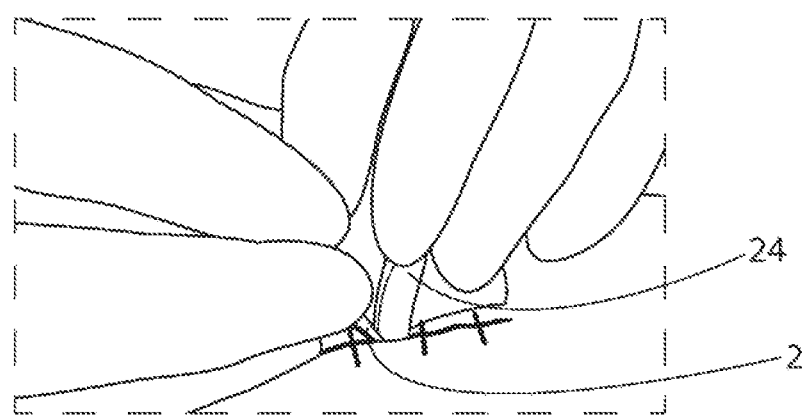

FIGS. 4G-4H shows the surgeon inserting another strip 24 into another gap 19 in the wound 15. Typically, the surgeon pushes the free end of the strip 24 down into the gap 19 and obtains a tactile indication to stop when the surgeon feels contact with the fascia layer is made.

Figure 4I:
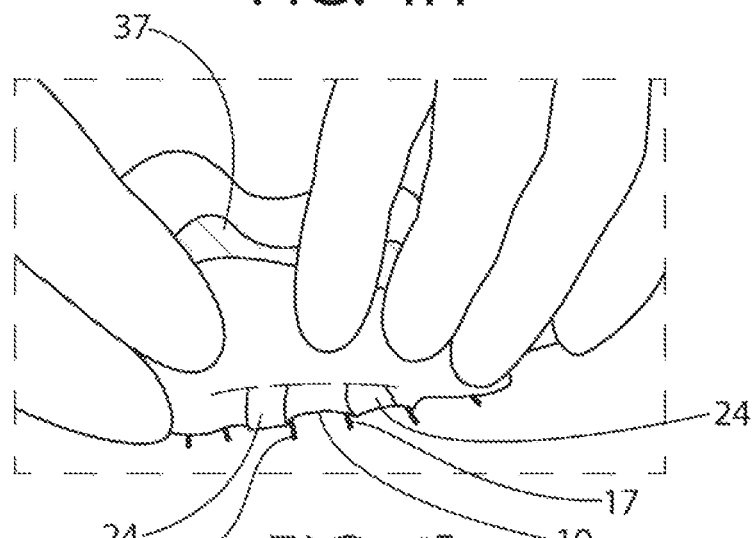

FIG. 4I shows both strips 24 pushed down into respective gaps 19 in the wound 15 between staples 17.

At this point, the surgeon needs only to secure the first portion (dressing) 22 down onto the skin 14 of the patient using the adhesive border. FIGS. 4J-4K show the surgeon applying the first portion 22 onto the skin 14 and then removes the release liner 36 from the first portion 22. FIG. 4M depicts the WHD 20/20A releasably secured in place in and over the wound 15. By way of example only, a transparent adhesive 37 overlays the top surface of the dressing 22 (and to which the release liner 36 was originally attached) that releasably secures the dressing 22 to the skin 14.

Figure 5:
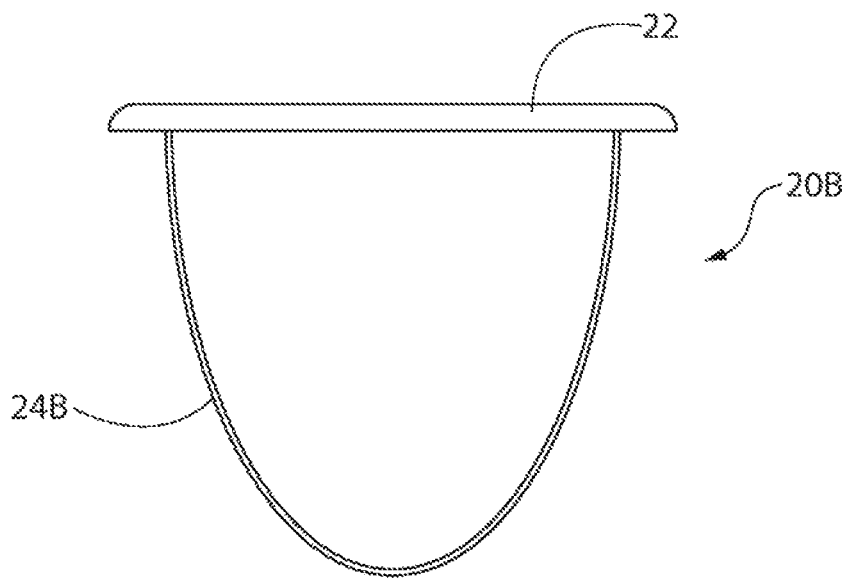
FIG. 5 depicts a third embodiment of the present invention which uses a continuous loop for the absorbent member that is disposed in the wound.

FIG. 5 depicts a third embodiment of the WHD 20B wherein the at least one strip 24 is replaced by a continuous absorbent member 24B that is formed into a large loop. The loop 24B comprises ends that correspond to ends of the first portion 22.

Figure 6:
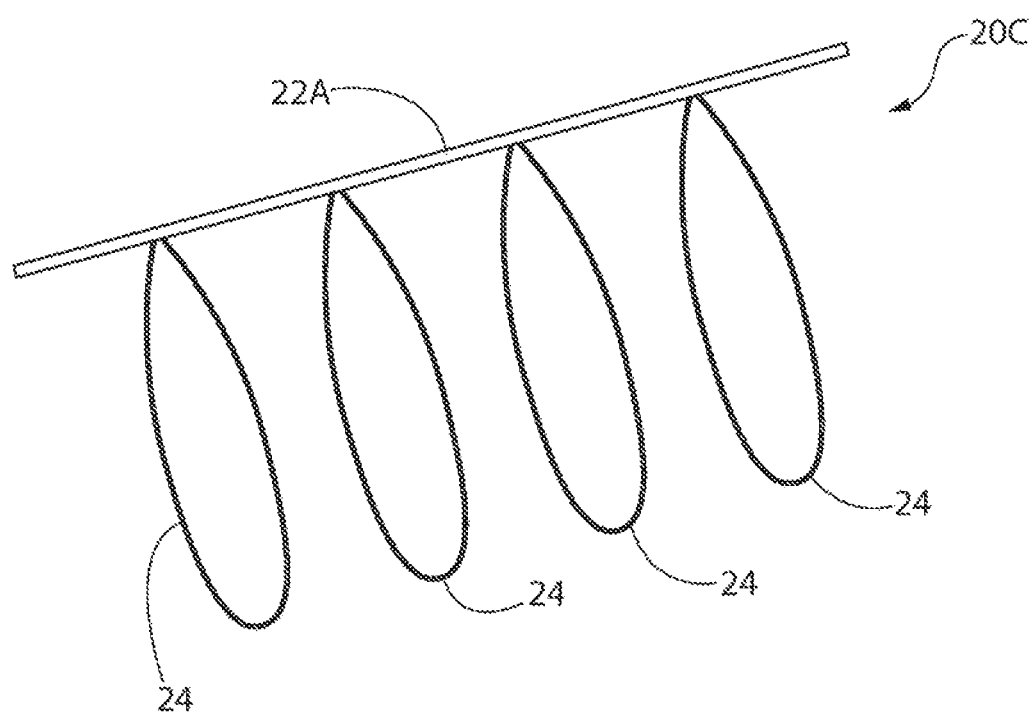
FIG. 6 depicts a fourth embodiment that uses a packing strip for the dressing and to which the absorbent members are coupled.

FIG. 6 depicts a fourth embodiment of the WHD 20C wherein the first portion 22 is formed of a thin packing material 22A.

Figure 7:
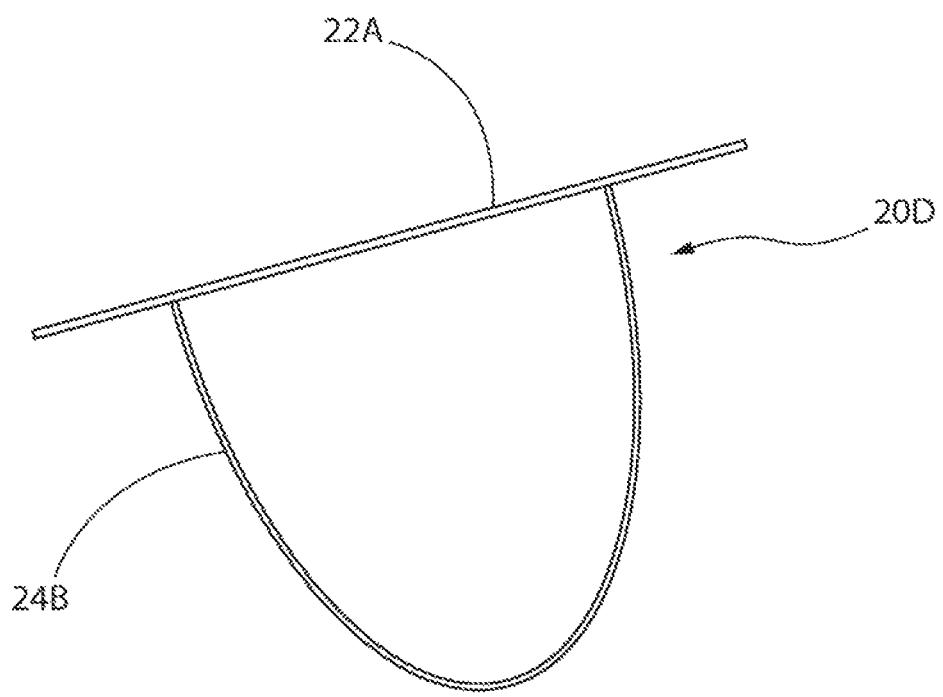
FIG. 7 depicts a fifth embodiment that uses a packing strip for the dressing and to which a continuous loop absorbent member is coupled.

FIG. 7 depicts a fifth embodiment of the WHD 20D which is a combination of the third and fourth embodiments. In particular, the first portion 22A is formed of a thin packing material 22A and the at least one strip 24 comprises the large loop 24B. As with the third embodiment 20B, the WHD 20D comprises the loop 24 having ends that correspond to the ends of the first portion 22.

Another key improvement to the WHD 20/20A is the ability to extend the length of the at least one strip 24A. This can be advantageous for a number of reasons. Allowing the surgeon to adjust the length of the at least one strip 24 permits the surgeon to customize the absorbing capability of the present invention 20 based on the patient's physiology. If, by way of example, the patient has a large girth, it may be necessary to extend the length of the at least one strip 24, deeper into the subcutaneous layer 16.

Figure 8:
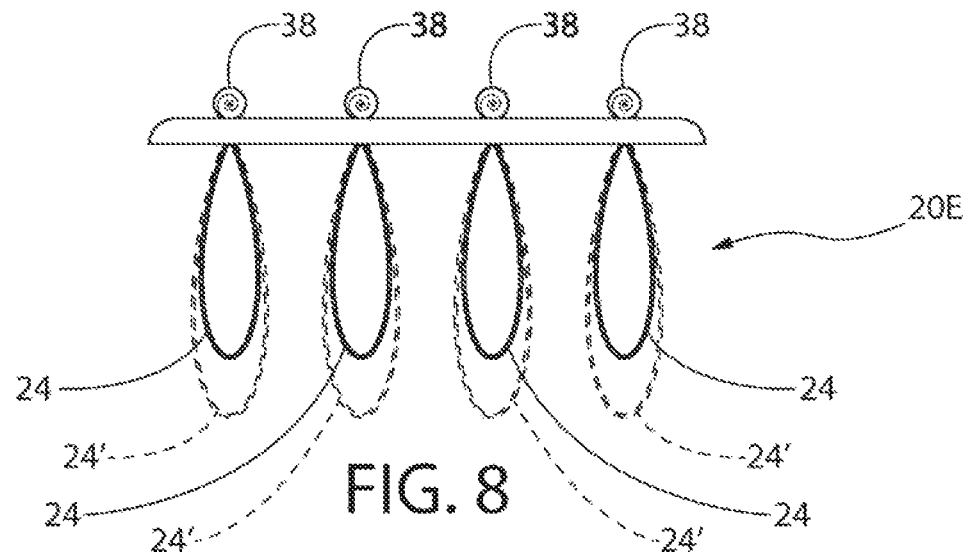
FIG. 8 depicts a sixth embodiment of the present invention that uses extendable absorbent members fed from respective dispensers on or from within the dressing.
Figure 9:
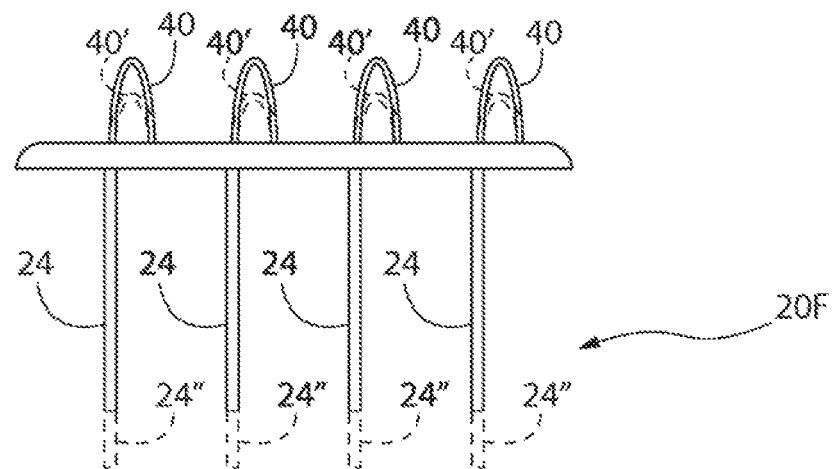
FIG. 9 depicts a seventh embodiment of the present invention that also uses extendable absorbent members that have extensions in the form of loops that pass through the present invention.
Figure 9A:
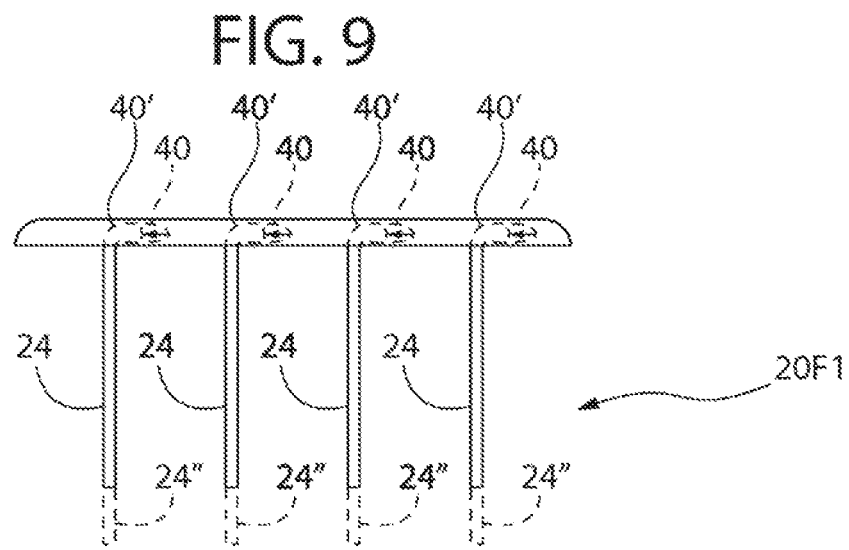
FIG. 9A depicts a variation of the seventh embodiment of the present invention that also uses extendable absorbent members that have extensions in the form of loops that are positioned within the bandage portion of the present invention.

To that end, FIG. 8 depicts a sixth embodiment 20E wherein respective cartridges 38 of strip material permit the strips 24 to be extended to new lengths 24', shown in phantom. Alternatively, FIG. 9 shows the use of "slack loops" 40 in a seventh embodiment 20F that project from the upper side of the first portion 22. Thus, when it becomes necessary to extend the lengths of the strips 24, the surgeon can push downward on each strip 24 to extend the length of each strip to that shown by 24" by a corresponding decrease 40' in the slack loops 40. It should be understood that the term "slack loops" in their broadest sense may include rolled, or folded or tucked fluid absorbent material strips that are located inside or outside the first portion 22; FIG. 9A shows an exemplary embodiment 20F1 where the "slack loops" are provided within the first portion 22 itself. The arrow indicates movement as the strip 24 is lengthened and the slack loops 40 are shortened.

Figure 10:
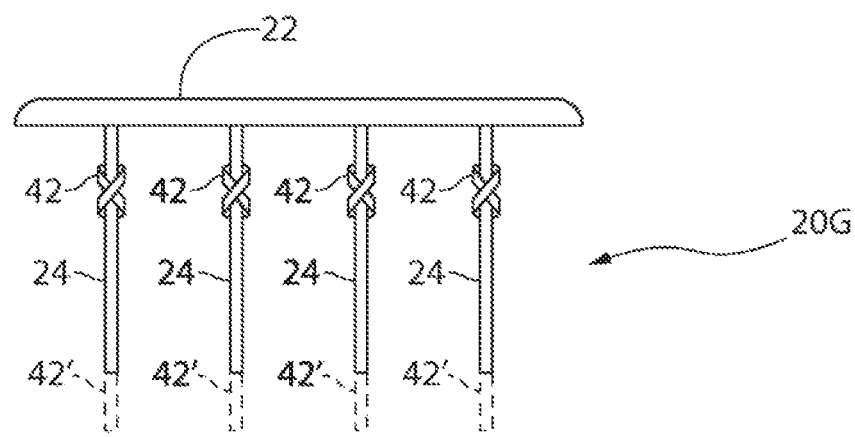
FIG. 10 depicts an eighth embodiment of the present invention that also uses extendable absorbent members wherein the extensions are formed from excess material formed into loops on the absorbent members.

FIG. 10 depicts an eighth embodiment 20G that uses "slip knots" 42 in each strip 24 that allow each strip 24 to be lengthened by applying a downward force on each strip 24; excess material formed in the slip know 42 permits the respective strip 24 to be lengthened 42'.

Figure 11:
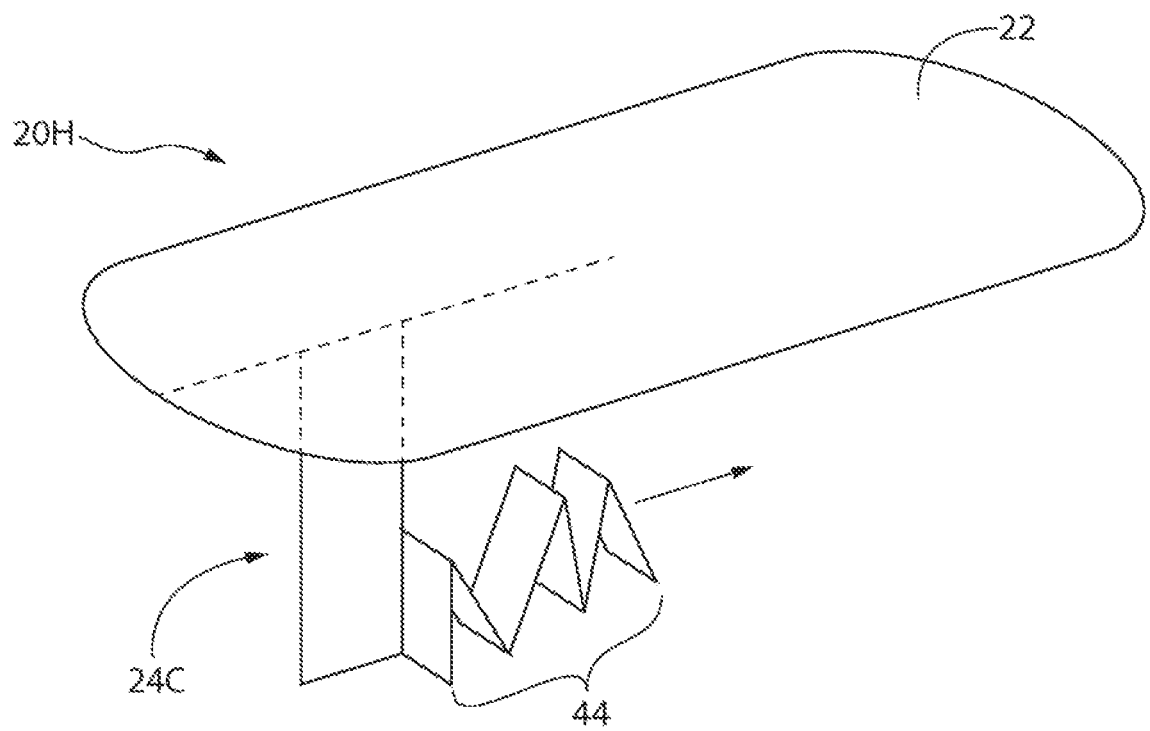
FIG. 11 depicts a ninth embodiment of the present invention wherein the absorbent member comprises foldable component that can be expanded into the wound once the absorbent member is passed into the closed incision.

FIG. 11 depicts a ninth embodiment 20H wherein the second portion 24C comprises a foldable portion 44 that can be expanded outward within the subcutaneous layer 16 once the second portion 24C is passed through a gap 19 in the wound 15. In particular, once the second portion 24 is pushed downward in the gap 19, the surgeon can then expand the foldable portion 44 along the length of the wound 15 within the subcutaneous layer 16.

Figure 13:
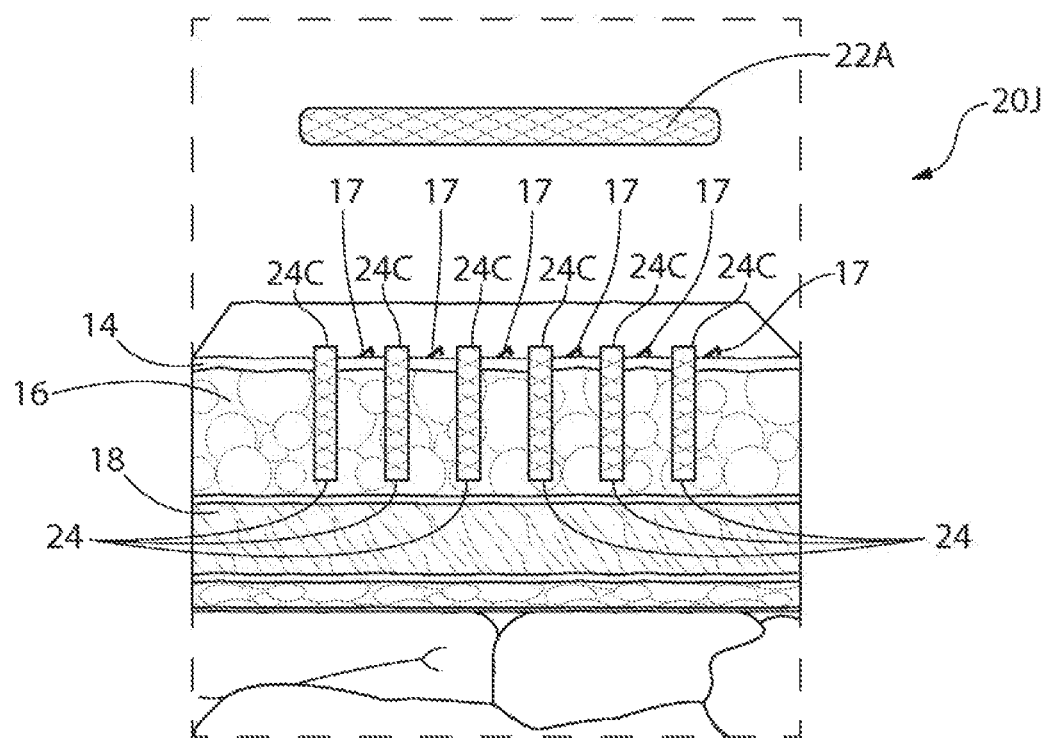
FIG. 13 depicts an eleventh embodiment of the present invention wherein the absorbent members are positioned within the wound without any coupling to a dressing and to which at a later stage a dressing may or may not be placed into contact with the portion of the absorbent members that extends out of the wound.

A further variation 20J of the present invention 20 is the use of free absorbent members 24 being placed into the wound in between the staples or sutures 17, wherein the upper ends 24C of the absorbent members are free, as shown most clearly in FIG. 13. In particular, the surgeon or other healthcare technician can insert each of these free absorbent members 24 in between the sutures or staples 17 in the subcutaneous layer tissue 16 above the muscle 18, as described previously. As also mentioned previously, these free absorbent members 24 may remain in the wound for approximately 1-3 days at which time they are then removed by the surgeon or other healthcare technician. As also mentioned earlier, fluids that form in the wound are absorbed by the strips 24 and are drawn upward, out of the skin layers 14/16. By removing fluid from these skin layers immediately, the chances for infection are greatly reduced. Furthermore, the fistulae 34 are also formed as described earlier with regard to FIG. 2. A separate dressing 22 may also be applied to the upper ends 24C during the time the free absorbent members 24 inserted into the wound, although this is not required.

Figure 14:
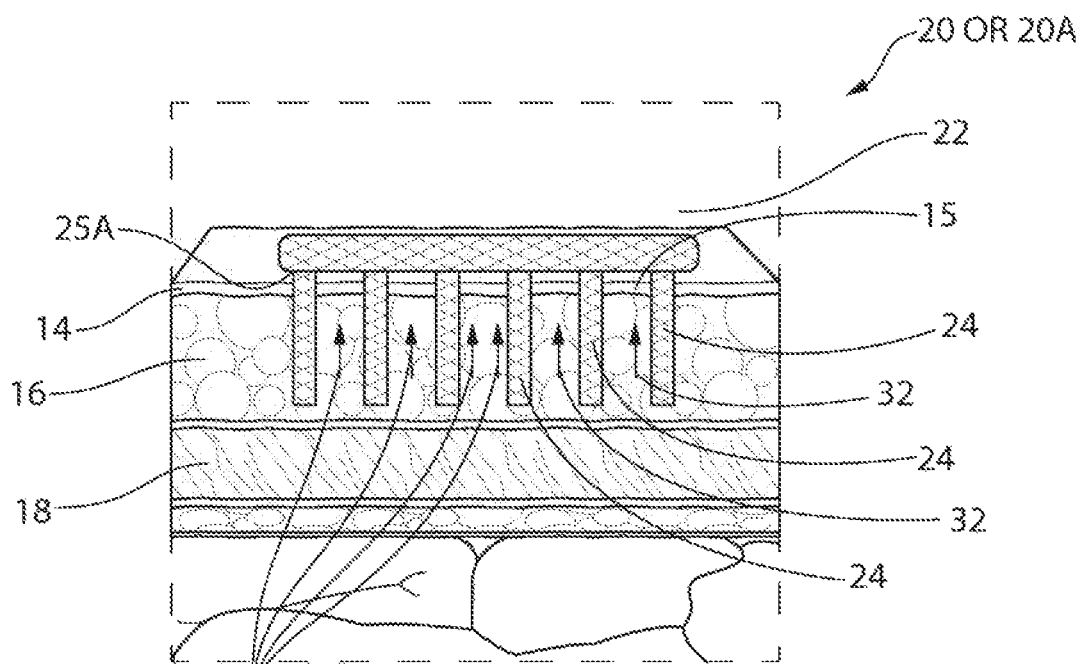
FIG. 14 is a functional diagram of the wound healing device in place in an open incision or wound (e.g., in a patient's abdominal wall)

It should be understood that it is within the broadest scope of the present invention to include the use of all of the embodiments of the WHD in open wounds also. By way of example only, as shown FIG. 14, the WHD 20 is placed inside an open wound, i.e., where no sutures or staples are used to close the wound. Thus, the surgeon places the strips 24 down into the open wound with the dressing 22 being placed at the skin level. Also by way of example only, the variation 20J discussed previously can be placed also into the open wound and then a separate dressing 22 may be placed in contact with the upper ends 24C of the free absorbent members 24.

Figure 15:
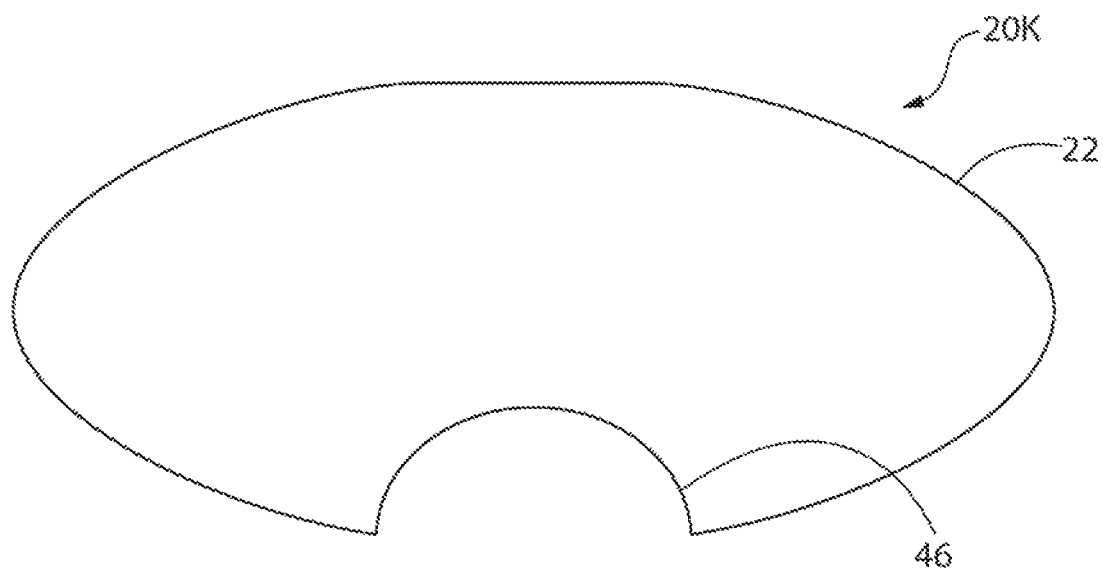
FIG. 15 is a plan view of the dressing of another variation of the wound healing device that includes a cutaway along its edge to accommodate an obstruction, such as a stoma, closely adjacent the incision or wound.
Figure 15A:
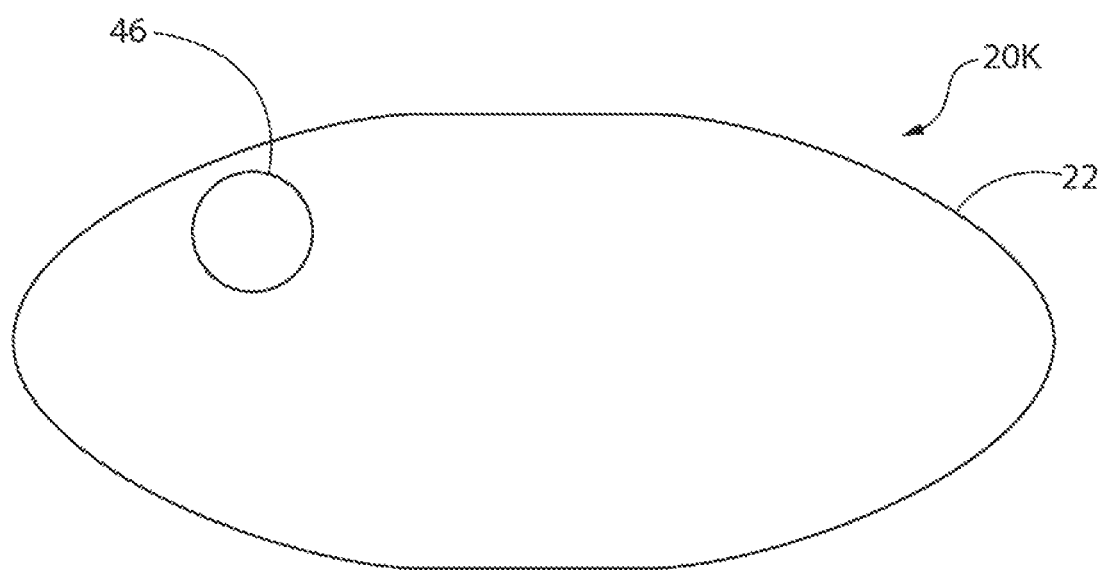
FIG. 15A is a plan view of a further embodiment of the wound healing device that includes an opening in the dressing that permits an obstruction to pass through the dressing to permit the dressing to make sufficient contact with the skin when the incision or wound is closely adjacent the obstruction.

FIGS. 15 and 15A provide further embodiments of the WHD to accommodate surrounding items or obstructions at the skin surface that would prevent the dressing 22 from making good contact with the skin surface. In particular, FIG. 15 depicts a top view of this additional WHD embodiment 20K whose first portion 22 comprises a dressing edge removed, forming a cutaway 46. For example, a where a patient has a stoma having a tube or other lumen that is coupled thereto and the wound or incision is closely adjacent that stoma, the WHD embodiment 20K can be positioned as described previously and the dressing 20 can be positioned such that the cutaway 46 is positioned closely adjacent the stoma/tube, thereby allowing the edges of the dressing 22 of the WHD 20K to make good contact with the skin surface and not be interfered with by the stoma/tube. It should be further understood that the shape of the cutaway 46 is by way of example only and it is not limited to a semi-circular contour but may comprise any shape and size. In addition, the relative position of the cutaway 46 can be located along any edge of the dressing 22.

FIG. 15A shows another embodiment 20L of the WHD wherein an interior portion forming an opening 48 of the dressing 22 is removed. Thus, where the incision or wound is located at a position closely adjacent some obstruction (e.g., a stoma, a tube, a medical device or sensor, etc.) that would prevent the dressing 22 from making sufficient contact with the skin surface, the obstruction (not shown) can be passed through the opening 48 to permit the dressing 22 to be positioned flush against the skin surface. Again, the opening 48 is shown by way of example only; other shapes and other locations on the dressing 22 may comprise the opening 48.

It should be noted that although not required, an anti-microbial composition may be applied to either the first portion 22 and/or the second portion 24.

Thus, the present invention relates to an apparatus/method of wound infection prevention and healing acceleration and life. The WHD 20 provides the effective post-surgical clean contaminated, contaminated, clean and infected incision when the rate of infection potential is considered significant. The apparatus/method may also be used in a variety of medical surgeries interventions and procedures. The present invention 20 can also be used in veterinary medicine.

The apparatus & method for wound infection device (WHD) 20 is useful for preventing SSI infection for the following surgeries including but is not limited to: general surgery procedures, colorectal, OBGYN procedures, urology, vascular surgeries, and neurosurgery procedures. The incisions or wounds closed following their respective surgeries are susceptible to high infection rates and slow patient recovery periods which also impact the physician, staff, hospital, insurer, etc. Moreover, SSI costs hospitals billions of dollars every year in the U.S. and insurance companies do not reimburse hospitals for maladies caused by infection, and corresponding complications, due to surgical site infection.

It should be further understood that the term WHD includes any all of kinds of kits that comprise the WHD and any associated components (e.g., a plurality of WHDs; tools that may be used by the surgeon to insert the second portion 24 into wound site (e.g., pliers, tweezers, dissectors, etc.) that are provided with the WHD 20 itself.

Thus, the apparatus and method for wound infection device (WHD) 20 accelerates the healing process by reducing the healing time by an average of 2 days per patient, which among other things, reduces hospital stay periods.

While the invention has been described in detail and with reference to specific examples thereof, it will be apparent to one skilled in the art that various changes and modifications can be made therein without departing from the spirit and scope thereof.

The invention claimed is:

1. An apparatus comprising:
a first fluid absorbent material with a first fluid absorbent characteristic configured to be applied external to a wound that is in a subcutaneous skin layer of a patient; and
a second fluid absorbent material with a second fluid absorbent characteristic in fluid communication with the first fluid absorbent material, wherein the second fluid absorbent material is configured to be positioned within the wound in the subcutaneous skin layer, and wherein the second fluid absorbent characteristic of the second fluid absorbent material is different than the first fluid absorbent characteristic so that the apparatus is configured to wick liquids in the wound in the subcutaneous skin layer from the second fluid absorbent material to the first fluid absorbent material.

2. The apparatus of claim 1, wherein the second fluid absorbent material is physically coupled to the first fluid absorbent material, such that the second fluid absorbent material cannot be left inside the subcutaneous skin layer when the first fluid absorbent material is removed from the patient.

3. The apparatus of claim 1, wherein the first fluid absorbent material includes an anti-microbial composition.

4. The apparatus of claim 1, wherein the second fluid absorbent material includes an anti-microbial composition.

5. The apparatus of claim 1, wherein the second fluid absorbent material comprises at least one strip that is stitched to the first fluid absorbent material.

6. The apparatus of claim 1, wherein the second fluid absorbent material is extendable.

7. The apparatus of claim 1, wherein there is a gap between the second fluid absorbent material and the first fluid absorbent material, such that the second fluid absorbent material does not directly contact the first fluid absorbent material.

8. The apparatus of claim 7, wherein the liquids cross the gap by capillary transfer from the second fluid absorbent material to the first fluid absorbent material.

9. The apparatus of claim 1, wherein the first fluid absorbent material and the second fluid absorbent material are composed of different materials.

10. An apparatus comprising:
a first fluid absorbent material configured to be applied external to a wound, wherein the wound is in a subcutaneous skin layer of a patient; and
a second fluid absorbent material in fluid communication with the first fluid absorbent material, wherein the first fluid absorbent material is configured to be positioned in the wound in direct contact with the subcutaneous skin layer to facilitate wicking of liquids and waste materials towards the first fluid absorbent material, the first fluid absorbent material with a first fluid-absorbing characteristic and the second fluid absorbent material with a second fluid-absorbing characteristic different than the first fluid-absorbing characteristic.

11. The apparatus of claim 10, wherein the second fluid absorbent material is physically coupled to the first fluid absorbent material, such that the second fluid absorbent material cannot be left inside the subcutaneous skin layer when the first fluid absorbent material is removed from the patient.

12. The apparatus of claim 10, wherein the second fluid absorbent material is one of a plurality of second fluid absorbent materials that are in fluid communication with the first fluid absorbent material.

13. The apparatus of claim 10, wherein the second fluid absorbent material comprises at least one strip that is stitched to the first fluid absorbent material.

14. The apparatus of claim 10, wherein the second fluid absorbent material is extendable.

15. The apparatus of claim 10, further comprising:
a spacer between the second fluid absorbent material and the first fluid absorbent material, such that the second fluid absorbent material does not directly contact the first fluid absorbent material, and wherein the liquids and waste materials transfer through the spacer to be absorbed by the first fluid absorbent material.

16. The apparatus of claim 10, wherein the first fluid absorbent material and the second fluid absorbent material are composed of different materials.

17. An apparatus comprising:
a first portion that is configured to be applied external to a subcutaneous skin layer of a patient, the first portion comprising a first fluid absorbent material; and
a second portion that is in fluid communication with the first portion at a first end of the second portion and second end of the second portion that is configured to be positioned within the subcutaneous skin layer, the second portion comprising a second fluid absorbent material, wherein the first fluid absorbent material with a first fluid-absorbing characteristic and the second fluid absorbent material with a second fluid-absorbing characteristic different than the first fluid-absorbing characteristic are configured for liquids in the subcutaneous skin layer to transfer from the second portion to the first portion, wherein there is a gap between the second fluid absorbent material and the first fluid absorbent material, such that the second fluid absorbent material does not directly contact the first fluid absorbent material.

18. The apparatus of claim 17, wherein the second fluid absorbent material is extendable.

19. The apparatus of claim 17, wherein beading of the liquids transfer from the second portion to the first portion.

20. The apparatus of claim 17, wherein transfer is realized by capillary transfer.

* * * * *